(12) United States Patent
Diemunsch

(10) Patent No.: US 8,118,769 B2
(45) Date of Patent: Feb. 21, 2012

(54) APPARATUS FOR CONDITIONING AN INSUFFLATION GAS

(75) Inventor: Pierre Diemunsch, Strasbourg (FR)

(73) Assignee: Storz Endoskop Produktions GmbH (DE)

( * ) Notice: Subject to any disclaimer, the term of this patent is extended or adjusted under 35 U.S.C. 154(b) by 1881 days.

(21) Appl. No.: 11/038,359

(22) Filed: Jan. 19, 2005

(65) Prior Publication Data

US 2005/0171466 A1    Aug. 4, 2005

Related U.S. Application Data

(63) Continuation of application No. PCT/EP03/07808, filed on Jul. 18, 2003.

(30) Foreign Application Priority Data

Jul. 19, 2002   (DE) ................................ 102 33 860

(51) Int. Cl.
*A61M 37/00* (2006.01)
(52) U.S. Cl. .......................... 604/25; 604/23
(58) Field of Classification Search ................ 604/23, 604/26, 82
See application file for complete search history.

(56) References Cited

U.S. PATENT DOCUMENTS

| | | | |
|---|---|---|---|
| 4,036,210 A * | 7/1977 | Campbell et al. ............. | 600/581 |
| 5,098,375 A | 3/1992 | Baier .............................. | 604/23 |
| 5,246,419 A | 9/1993 | Absten ............................ | 604/26 |
| 5,411,474 A * | 5/1995 | Ott et al. ........................ | 604/26 |
| 5,423,741 A * | 6/1995 | Frank ............................... | 604/26 |
| 5,483,953 A * | 1/1996 | Cooper ..................... | 128/200.22 |
| 5,599,297 A * | 2/1997 | Chin et al. ...................... | 604/26 |
| 5,660,167 A * | 8/1997 | Ryder ....................... | 128/200.21 |
| 5,752,502 A * | 5/1998 | King ......................... | 128/200.18 |
| 5,875,774 A * | 3/1999 | Clementi et al. ......... | 128/200.18 |
| 6,010,118 A | 1/2000 | Milewicz ...................... | 261/142 |
| 6,068,609 A * | 5/2000 | Ott et al. ......................... | 604/26 |
| 6,223,745 B1 * | 5/2001 | Hammarlund et al. .. | 128/200.18 |
| 6,244,219 B1 * | 6/2001 | Krum ............................ | 119/245 |
| 6,269,810 B1 * | 8/2001 | Brooker et al. .......... | 128/203.12 |
| 6,510,846 B1 * | 1/2003 | O'Rourke ................ | 128/200.21 |
| 6,544,210 B1 * | 4/2003 | Trudel et al. .................... | 604/26 |
| 6,581,600 B2 * | 6/2003 | Bird .......................... | 128/205.24 |

(Continued)

FOREIGN PATENT DOCUMENTS

DE    27 35 028    3/1978

(Continued)

OTHER PUBLICATIONS

K. Semm, Die Laparoskopie in der Gynakologie, Nov. 1967, Geburtshilfe and Frauenheilkunde, vol. 11, pp. 1029-1042.

(Continued)

*Primary Examiner* — Nicholas Lucchesi
*Assistant Examiner* — Victoria P Campbell
(74) *Attorney, Agent, or Firm* — St. Onge Steward Johnston & Reens LLC

(57) ABSTRACT

An apparatus for conditioning an insufflation gas has an inlet for the delivery of an insufflation gas to a conditioning chamber. The conditioning chamber is used to charge the insufflation gas with a medicament by blowing the insufflation gas through a humidifying liquid containing the medicament. The insufflation gas charged with the medicament flows from the charging device to an outlet and can be delivered to the abdominal cavity of a human or animal, where it ensures optimum distribution of the medicament.

11 Claims, 1 Drawing Sheet

U.S. PATENT DOCUMENTS

Figure 1:
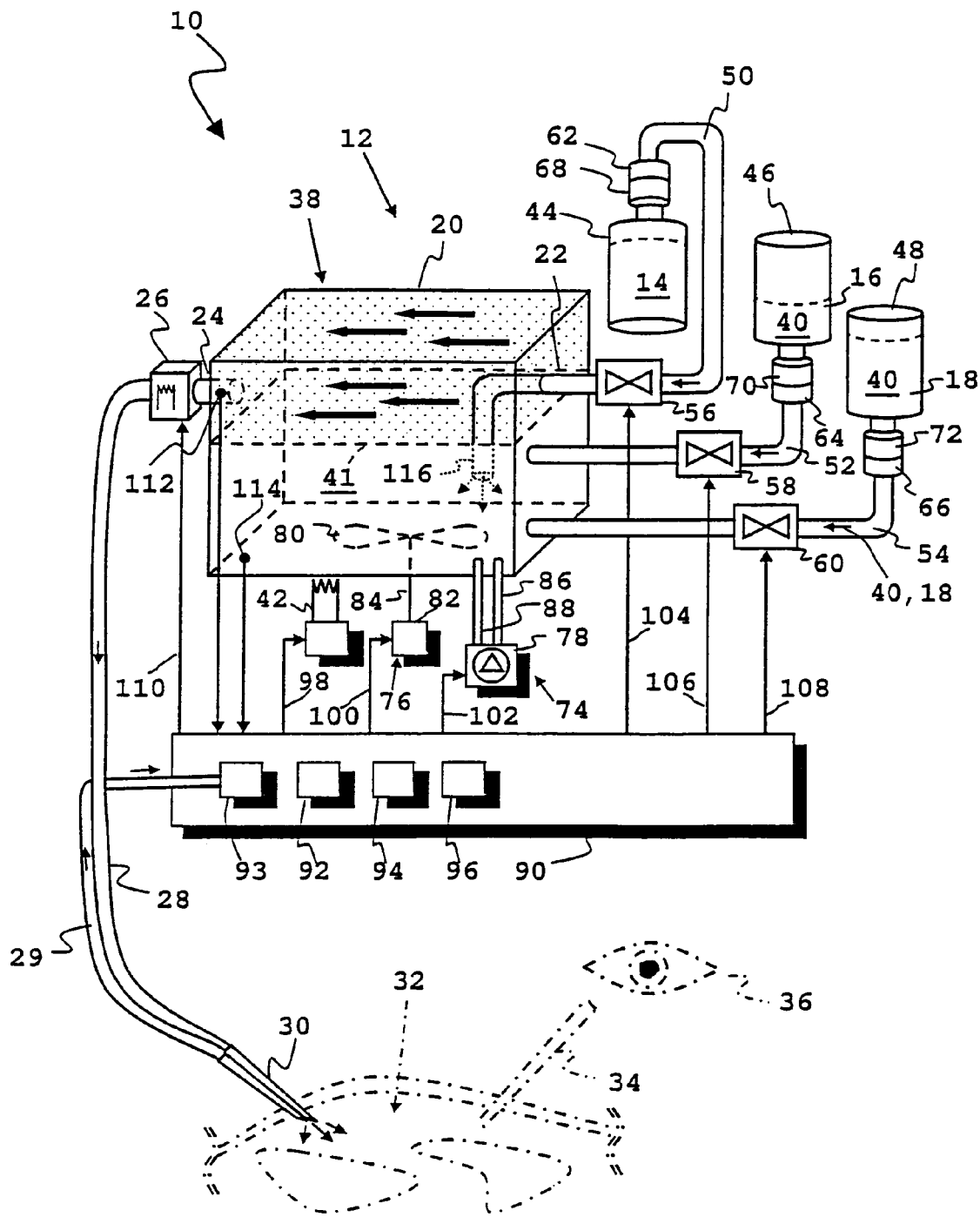

| | | | |
|---|---|---|---|
| 6,595,203 B1* | 7/2003 | Bird | 128/200.21 |
| 6,609,515 B2* | 8/2003 | Bienvenu et al. | 128/200.21 |
| 6,679,250 B2* | 1/2004 | Walker et al. | 128/200.21 |
| 2002/0073991 A1* | 6/2002 | Gonda | 128/200.22 |
| 2003/0010344 A1* | 1/2003 | Bird | 128/205.24 |
| 2003/0014004 A1* | 1/2003 | Dey | 604/26 |
| 2006/0064257 A1* | 3/2006 | Pennington et al. | 702/50 |

FOREIGN PATENT DOCUMENTS

| | | |
|---|---|---|
| DE | 39 22 746 C1 | 8/1990 |
| DE | 195 10 710 A1 | 9/1996 |
| DE | 296 12 115 U1 | 9/1996 |
| DE | 693 25 037 T2 | 1/2000 |
| EP | 0 684 850 B1 | 5/1999 |
| EP | 0 937 478 A1 | 8/1999 |

OTHER PUBLICATIONS

P. Diemunsch, D. Mutter, R. Schaeffer, D. Graff, F. Hirezi, J. Marescaux; Central Body Temperature During Prolonged Laparoscopy Decreases Despite Heating of the Insulfflated CO2; Hopitaux Universitaries, Strasbourg, France, 1 page.

* cited by examiner

APPARATUS FOR CONDITIONING AN INSUFFLATION GAS

CROSS-REFERENCE OF PENDING APPLICATION

This application is a continuation of pending international application PCT/EP2003/007808 filed on Jul. 18, 2003 which designates US and which claims priority of German patent application No. 102 33 860.4 filed on Jul. 19, 2002.

BACKGROUND OF THE INVENTION

The invention relates to an apparatus for conditioning an insufflation gas.

An important principle for endoscopic viewing of the abdominal cavity of a human or of an animal is the creation of a gas-inflated space within the respective abdominal cavity. An insufflator is used to pump an insufflation gas into the abdominal cavity, by which the abdominal cavity is inflated. In any event, the insulated gas creates the viewing or operating space which is needed between the internal organs and the abdominal wall to permit examination or surgery. The insulation gas normally used is carbon dioxide gas.

A device for introducing insufflation gas into the abdominal cavity is known, for example, from the article entitled "Die Laparoskopie in der Gynätkologie" by K. Semm in "Geburtshilfe und Frauenheilkunde", volume 11, November 1967. With this device, it is possible to control and monitor the quantity and the pressure of the insufflation gas flowing into the abdominal cavity via an insulation cannula.

In order to avoid postoperative pain and complications, or at least to reduce these, the insulation gas is humidified. To this end, the insufflation gas is sometimes also heated. In connection with this it has been found that the humidification of the insufflation gas is important. By contrast, additional heating of the insufflation gas affords no real added benefit. This is known, for example, from the publication entitled "Central body temperature during prolonged laparoscopy decreases despite heating of the insufflated $CO_2$" by P. Diemunsch, D. Multer, R. Schaeffer, D. Graff, F. Hirezi and J. Marescaux.

In connection with endoscopic examinations, it is in many cases necessary or desirable to administer medicaments with an antibacterial, anti-inflammatory, local anaesthetic or anti-carcinogenic action to the patent. These medicaments can, for example, be administered systemically through the bloodstream. However, this has the disadvantage that the medicament administration is not restricted to the area of the abdomen, and instead takes place throughout the body. Another possible way of administering a medicament is to introduce the medicament into the abdomen in the form of a mixture with an irrigation fluid. Although the medicament administration is then restricted to the abdomen, only the tissue surfaces contacted by the irrigation fluid are reached. In addition, it is often not necessary for an irrigation fluid to be used.

It is therefore an object of the present invention to permit the administration of one or more medicaments in connection with a medical intervention in which the abdominal cavity of a human or of an animal is filled with an insufflation gas.

SUMMARY OF THE INVENTION

According to the invention, this object is achieved by an apparatus for conditioning an insufflation gas comprising a conditioning chamber, at least one first inlet for delivering a humidifying liquid containing a medicament, a second inlet for blowing an insulation gas into said humidifying liquid containing said medicament contained in said conditioning chamber, an outlet for dispensing said insulation gas charged with said humidifying liquid containing said medicament, and a blowing device for blowing said insufflating gas through said chamber.

In an apparatus according to the invention the insufflation gas is blown by the blowing device through the humidifying liquid containing a medicament. The insufflation gas thereby picks up minute droplets of the humidifying liquid containing a medicament and therefore is humidified and charged with the medicament.

According to the invention, the insufflation gas thus has multiple functions: It serves, in a manner known per se, to form an inflated space in the abdominal area of a human or of an animal, so that the necessary viewing space for an endoscopic intervention is created there. In addition, the insufflation gas serves as a carrier for at least one medicament.

The insufflation gas reaches branched and narrow regions of the abdominal area and thus ensures optimum distribution of the medicament with which it is charged. The insulation gas, assisted by the pressure at which it is set, also diffuses into narrowly branched tissue parts. The medicament administration takes place locally in the abdominal area. In this way, one or more medicaments can be administered in a targeted manner, effectively, and at the smallest possible dosage. By this means, side effects can also be reduced or even completely avoided. Medicament administration systemically through the bloodstream, for example, is then no longer necessary, which greatly simplifies treatment.

The medicaments can, for example, be antibacterial medicaments, anti-inflammatory medicaments, local anesthetics or anti-carcinogenic medicaments. It will be appreciated that the insufflation gas can also be charged, in the manner according to the invention, with active substance combinations. Medicaments in gaseous form, liquid form and solid form can be used.

A liquid form can contain the medicament as it is, insofar as this is liquid, but it can also be present as a solution or as an emulsion.

A solid medicament can be dissolved in the humidifying liquid, but can also be present as a suspension or a slurry.

The apparatus according to the invention can be an add-on device for an insufflator with which the delivery of an insufflation gas to an abdominal area can be controlled and monitored. However, it is also possible for these functions to be taken over by the apparatus according to the invention itself, i.e. for the apparatus according to the invention to be designed as an insufflator. The apparatus then has, for example, a charging device according to the invention for charging the insufflation gas with a medicament, and a gas control device for controlling a physical condition, for example the quantity and/or the pressure of the insufflation gas delivered to the outlet. The insufflator can act as the blowing device providing the energy, i.e. the pressure, for moving the insufflation gas through the apparatus of the invention.

It will be appreciated that the features mentioned above and the features still to be explained below can be used not only in the stated combinations, but also in other combinations or in isolation, without departing from the scope of the present invention.

BRIEF DESCRIPTION OF THE DRAWING

The invention is described and explained in greater detail below on the basis of a selected illustrative embodiment and with reference to the attached drawing, in which:

FIG. 1 shows a perspective view, very diagrammatically in part, of an illustrative embodiment of an apparatus according to the invention for conditioning an insufflation gas.

DETAILED DESCRIPTION OF PREFERRED EMBODIMENT

In FIG. 1, an illustrative embodiment of an apparatus for conditioning an insufflation gas is indicated in its entirety by reference number 10. The apparatus 10 according to this illustrative embodiment forms an insufflator with which an insufflation gas can be delivered to an abdominal cavity of a human or animal.

The apparatus 10 has a charging device 12 for charging an insufflation gas 14 with medicaments 16 and 18. The charging device 12 includes a conditioning chamber 20 into which medicaments 16 and 18 can flow via two first inlets and into which the insufflation gas 14 can flow via a second inlet 22. The insulation gas 14 charged with the medicaments 16, 18 can flow out of the conditioning chamber 20 via an outlet 24. A heater 26 for heating the insufflation gas 14 is arranged at the outlet 24. From the heater 26, the insufflation gas 14 charged with the medicaments 16, 18 can flow to an insufflation cannula 30 via a line 28 designed as a tube. Via the insulation cannula 30 which is, for example, an insulation needle, the insufflation gas 14 can flow into an abdominal area 32 of a human or animal. A space inflated by the insufflation gas is thus created in the area 32, so that endoscopic examinations or surgical treatments can be carried out therein by an operating physician 36 with the aid of a diagrammatically indicated endoscope 34.

The apparatus 10 is designed to humidify the insufflation gas 14. Accordingly, the charging device 12 includes a humidifying device 38 which serves to humidify the insufflation gas 14 with a humidifying liquid 40 which contains the medicaments 16 and 18.

The conditioning chamber 20, which in the present illustrative embodiment forms a humidifying chamber, is represented very diagrammatically in the drawing as a hollow cube. A humidifying liquid bath 41 containing the humidifying liquid 40 is located in the lower area of the conditioning chamber 20. The medicaments 16 and 18 are dissolved in the humidifying liquid 40.

The humidifying liquid 40 can be heated with a heating element 42. By charging it with the heated humidifying liquid 40, the insufflation gas 14 is additionally heated and is adapted optimally to the microclimate present in the abdominal area 32. The advantageously provided heater 26 ensures a reheating of the insufflation gas 14, although this is not absolutely necessary.

The insufflation gas 14 is, for example, carbon dioxide ($CO_2$). The medicament 16 is, for example, an antibacterial medicament, and the medicament 18 an anti-inflammatory medicament. The two medicaments 16, 18 are each dissolved in the humidifying liquid 40, which is sterile water for example. "Dissolved" must here be understood in a very broad sense, because the medicaments 16, 18 can, for example, also be present in the humidifying liquid 40 in the form of emulsions or slurries.

Storage vessels 44, 46, 48 are provided, for the insufflation gas 14 and for the medicaments 16 and 18 dissolved in the humidifying liquid 40, respectively, and these storage vessels 44, 46, 48 are connected to the conditioning chamber 20 via lines 50, 52 and 54, respectively. Arranged on the lines 50, 52, 54, there are dosing devices 56, 58, 60 with which it is possible to adjust the flow of the insufflation gas 14 and of the humidifying liquid 40 with the medicaments 16 and 18. The dosing devices 56 through 60 are valve arrangements for example. The dosing device 56 includes, for example, a pressure control, safety valves, venting valves or the like. The dosing device 56 serves to reduce and adjust the pressure of the insufflation gas 14 which is present in the storage vessel 44 at a high pressure of ca. 5-60 bar. The humidifying liquid 40 is supplied to the conditioning chamber 20 to a level at which an opening or mouth of the line 50 is immersed into the humidifying liquid bath 41.

At this point it will be noted that the "conditioning" of the insufflation gas 14, namely the humidifying and the charging with the medicaments 16 and 18 in the apparatus 10, preferably takes place on the low-pressure side. Accordingly, the pressure-reducing dosing device 56 is located upstream of the conditioning chamber 20. It is further preferred that the "conditioning" of the insufflation gas 14 takes place as close as possible to the outlet of the apparatus 10. The conditioning chamber 20 is therefore situated close to the line 28.

In the drawing, the storage vessels 44, 46, 48 are shown in greatly simplified form and are identical. They are arranged on the charging device 12 in such a way as to be exchangeable. In principle, however, instead of the exchangeable storage vessels 44 through 48, it would also be possible to provide refillable storage vessels which are connected permanently to the apparatus 10. In the illustrative embodiment, the storage vessels 44, 46, 48 are cartridges. Arranged on the lines 50, 52, 54, there are respective connectors 62, 64, 66 to which the storage vessels 44, 46, 48 can be secured via mating connectors 68, 70, 72. The connectors 62, 64, 66 form together with the corresponding mating attachment pieces 68, 70, 72, for example bayonet connections or screw connections. An empty storage vessel 44, 46, 48 can easily be replaced by a full storage vessel. The connectors 62, 64, 66 can each be individually coded in order to avoid incorrect attachment of a storage vessel 44, 46, 48 with unsuitable content.

As has already been explained, the medicaments 16, 18 can be present in the form of emulsions or slurries in the humidifying liquid 40. A distributing element 74 arranged at the conditioning chamber 20 distributes the medicaments 16, 18 uniformly in the humidifying liquid 40 and thus prevents sediment formation. The distributing element 74 includes a stirring device 76 and a circulating pump 78.

The stirring device 76 has a stirring propeller 80 which is arranged in the lower area of the conditioning chamber 20 and which is driven by an electric motor 82 by way of a shaft 84.

The circulating pump 78 is connected to the lower area of the conditioning chamber 20 via lines 86 and 88. The circulating pump 78 for example, sucks the humidifying liquid 40 through the line 86, and pumps it back into the conditioning chamber 20 through the line 88. A flow is thus established, inside the conditioning chamber 20, which results in a fine distribution of the medicaments 16, 18 in the humidifying liquid 40.

It will be appreciated that the distributing element 74 could include only the stirring device 76 or the circulating pump 78. Moreover, other embodiments of the distributing element 74 are also possible. They could, for example, include a slide which moves to and fro in the lower area of the conditioning chamber 20.

The functions of the apparatus 10 are controlled and monitored by a central control unit 90. The control unit 90 forms, on the one hand, a gas control device for controlling the quantity and the pressure of the insufflation gas 14 delivered to the outlet 24, and, on the other hand, a dose control device for dosing the proportion of the humidifying liquid 40 and of the medicaments 16 and 18 in the insufflation gas 14.

The control unit 90 is, for example, a microprocessor control with a microprocessor 92. The control unit 90 has output devices 94, for example a display and a speaker, and input devices 96, for example function keys. The control unit 90 controls and monitors the heating element 42, the stirring device 76, the circulating pump 78 and the dosing devices 56, 58 and 60 via control lines 98, 100, 102, 104, 106, 108. The control unit 90 also controls the heater 26 via a control line 110.

To generate the control signals transmitted via the control lines 98 through 110, status report information is required, for example concerning pressure, temperature, humidity, filling level or the like. To generate and transmit such status report information, sensors are provided, of which sensors 112 and 114 are shown by way of example.

The sensor 112 is arranged at the outlet 24 and reports to the control unit 90 to what extent the insufflation gas 14 is saturated with the humidifying liquid 40 and with the medicaments 16, 18. Accordingly, the control unit 90 can control the heating element 42, for example, to increase or decrease the heating of the humidifying liquid 40.

The sensor 114 is arranged in the lower area of the conditioning chamber 20 and reports to the control unit 90, for example, the proportion of the medicament 16 in the humidifying liquid 40 which is located in the conditioning chamber 20. Accordingly, the control unit 90 can, for example, control the dosing device 58.

In the illustrative embodiment described above in connection with the apparatus 10, the humidifying liquid 40 is heated, which on the one hand leads to a certain evaporation effect of the humidifying liquid 40 and on the other hand permits optimum adaptation of the insufflation gas 14 to the microclimate conditions prevailing in the abdominal area 32, that is to say to the temperature therein and to the humidity prevailing there.

However, there are also medicaments which must be exposed to the least possible thermal stress. An apparatus according to the invention is particularly suited for such medicaments.

The apparatus 10 according to the invention comprises a blower device which is in this case arranged at the second inlet 22. In the present case, the blower device has a line section 116 which is curved in the direction of the lower area of the conditioning chamber 20 and which opens into the humidifying liquid bath 41. The pressurized insufflation gas 14 flowing from the storage vessel 44 is accordingly blown into the humidifying liquid 40. The insufflation gas 14 passing through the humidifying liquid 40, picks up small quantities of the latter and of the medicaments 16, 18 contained therein and flows to the outlet 24. The insufflation gas 14 is as it were guided through the humidifying liquid bath 41.

A gas withdrawal line 29 is provided through which gas can be withdrawn again from the abdominal area 32 and delivered to a measuring device 93. The measuring device 93 has a pressure sensor which measures the pressure of the gas in the abdominal area. The signal generated by the sensor is fed to the dosing device 56 for controlling the quantity of insufflation gas to be delivered.

What is claimed is:

1. An apparatus for conditioning an insufflation gas comprising:

a conditioning chamber having at least one first inlet for delivering a humidifying liquid containing a medicament into said conditioning chamber, a second inlet for blowing an insufflation gas into said humidifying liquid containing said medicament contained in said conditioning chamber, and an outlet for dispensing said insufflation gas charged with said humidifying liquid containing said medicament, and a blowing device for blowing said insufflating gas through said chamber, wherein said conditioning chamber further comprises distributing elements for distributing said medicament in said humidifying liquid.

2. Apparatus of claim 1, wherein a dosing device for a dosed delivery of said medicament to said conditioning chamber is provided.

3. Apparatus of claim 1, wherein said outlet has a dose control device for controlling a proportion of said humidifying liquid containing said medicament in said insufflation gas.

4. Apparatus of claim 1, wherein said distributing elements comprise at least one of a stirring device for stirring said humidifying liquid and a circulating pump for circulating said humidifying liquid and said medicament.

5. Apparatus of claim 1, wherein temperature control elements for controlling a temperature of said humidifying liquid are provided.

6. Apparatus of claim 5, wherein said temperature control elements comprise heating elements for heating said humidifying liquid.

7. Apparatus of claim 1, wherein a gas control device for controlling at least one physical condition of said insufflation gas delivered through said outlet is provided.

8. Apparatus of claim 1, wherein said outlet is connected to an insufflation cannula.

9. Apparatus of claim 8, wherein said insufflation cannula has a withdrawal line for withdrawing gas from a body cavity through which withdrawal line said gas can be delivered to a measuring device.

10. Apparatus of claim 1, wherein said first inlet is connected to a supply line having a connector for an exchangeable storage vessel for storing said humidifying liquid containing said medicament.

11. Apparatus of claim 1, wherein said distributing elements include a circulating pump having an inlet tube and an outlet tube, each of said tubes leading from said circulating pump into said conditioning chamber for circulating the humidifying liquid.

* * * * *